(12) United States Patent
Robinson et al.

(10) Patent No.: US 7,280,204 B2
(45) Date of Patent: Oct. 9, 2007

(54) MULTI-SPECTRAL DETECTOR AND ANALYSIS SYSTEM

(75) Inventors: Joseph Paul Robinson, West Lafayette, IN (US); Bartlomiej Rajwa, West Lafayette, IN (US); Gérald Grégori, Marseille (FR); Valery Patsekin, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 139 days.

(21) Appl. No.: 11/101,717

(22) Filed: Apr. 8, 2005

(65) Prior Publication Data

US 2005/0275839 A1 Dec. 15, 2005

Related U.S. Application Data

(60) Provisional application No. 60/613,175, filed on Sep. 23, 2004, provisional application No. 60/612,382, filed on Sep. 22, 2004, provisional application No. 60/560,828, filed on Apr. 8, 2004.

(51) Int. Cl.
 *G01J 3/30* (2006.01)
(52) U.S. Cl. .................... 356/318; 356/72; 356/73; 356/306; 356/311
(58) Field of Classification Search .............. 356/318, 356/306, 311
See application file for complete search history.

(56) References Cited

U.S. PATENT DOCUMENTS

| 4,857,451 | A | | 8/1989 | Schwartz .................. 435/7.24 |
| 4,905,169 | A | | 2/1990 | Buican ....................... 356/365 |
| 5,029,023 | A | * | 7/1991 | Bearden et al. ............... 369/69 |
| 5,394,237 | A | | 2/1995 | Chang et al. ............. 188/79.51 |
| 5,422,712 | A | | 6/1995 | Ogino ......................... 356/73 |
| 5,675,517 | A | | 10/1997 | Stokdijk ...................... 702/85 |
| 5,719,667 | A | * | 2/1998 | Miers ......................... 356/73 |
| 6,249,341 | B1 | * | 6/2001 | Basiji et al. .................. 356/73 |
| 6,630,307 | B2 | * | 10/2003 | Bruchez et al. ............... 435/6 |
| 6,885,440 | B2 | * | 4/2005 | Silcott et al. ................ 356/73 |
| 6,947,134 | B2 | * | 9/2005 | Chang et al. ............... 356/318 |
| 7,057,712 | B2 | * | 6/2006 | Beck et al. .................. 356/72 |

(Continued)

FOREIGN PATENT DOCUMENTS

EP 0 315 939 5/1989

(Continued)

OTHER PUBLICATIONS

Yong Feng et al., Model of a TDI line scan camera and its electronics, The 29th Annual Conference of the IEEE Industrial Electronics Society, 2003 IECON '03, vol. 3, Nov. 2-6, 2003, pp. 2215-2220.*

(Continued)

*Primary Examiner*—Gregory Toatley, Jr.
*Assistant Examiner*—Scott M Richey
(74) *Attorney, Agent, or Firm*—Brinks Hofer Gilson & Lione

(57) ABSTRACT

A multi-spectral detection and analysis system detects and classifies a targeted sample. The system may include a light source that causes the targeted sample to luminesce. A light dispersion element disperses the luminescence to a photodetector in a photodetector array. Each photodetector in the array transmits a signal indicating a portion of the spectrum to a multi-channel collection system. The multi-channel collection system processes the signal into a digital signal and forms the digital signal into a spectral signature. A processor analyzes the spectral signature and compares the spectral signature to known spectral signatures to identify the targeted sample.

34 Claims, 6 Drawing Sheets

U.S. PATENT DOCUMENTS

2003/0098422 A1* 5/2003 Silcott et al. ............ 250/458.1
2005/0274915 A1* 12/2005 Holcomb et al. ........... 250/577

FOREIGN PATENT DOCUMENTS

JP          63173578        7/1998

OTHER PUBLICATIONS

Fluorescence Staining and Flow Cytometry for Monitoring Microbial Cells, D.A. Veal, D. Deere, B. Ferrari, J. Piper, P.V. Attfield, Journal of Immunological Methods 243 (2000), pp. 191-210.

Observation of Single-Cell Fluorescence Spectra in Laser Flow Cytometry, M.R. Gauci, G. Vesey, J. Narai, D.Veal, K.L. Williams, J.A. Piper, Cytometry 25:388, 1996, pp. 388-393.

H.B. Steen and T. Stokke: "Fluorescence spectra of cells stained with a DNA—specific dye, measured by flow of cytometry," Department of Biophysics, Norsk Hydro's Institute for Cancer Research, Montebello, 0310 Oslo 3 Norway, Cytometry 7, pp. 104-106 (1986).

C.G. Wade et al.: "Spectra of cells in flow cytometry using a vidicon detector," J Histochem Cytochem 27, pp. 1049-1052 (1979).

* cited by examiner

Classification of microparticles based on Principal Components Analysis

MULTI-SPECTRAL DETECTOR AND ANALYSIS SYSTEM

PRIORITY CLAIM

This application claims the benefit of U.S. Provisional Application Nos. 60/560,828 filed on Apr. 8, 2004, 60/612,382 filed on Sep. 22, 2004, and 60/613,175 filed on Sep. 23, 2004. The above provisional applications are incorporated herein by reference.

BACKGROUND OF THE INVENTION

1. Field of the Invention

This invention relates to multi-spectral detectors of luminescence, and in particular to the detection of luminescence from materials that are stimulated with light sources.

2. Background of the Invention

Multi-spectral detector systems may detect luminescence from particles and materials that are stimulated with a light source. Such systems may further analyze the luminescence. Multi-spectral systems may include a flow cytometry system that characterizes and classifies particles of interest from heterogeneous populations. Flow cytometry interrogates a particle suspended within a stream of liquid as the particle passes through a light focusing on a small region. Early flow cytometers measured only light scatter and Coulter volume with minimal ability to measure fluorescence. Later, flow cytometers began to collect the fluorescence emission of light in the visible spectrum that might represent the presence of various chemical or biological components. The flow cytometers analyze single micro-particles and/or cells, separating the micro-particles and/or cells into populations based upon statistical differences of intensity measurements from each particle/cell.

Single-cell detection systems use screening devices that detect light emitted by a particle after its excitation by a light source and split the light into different pathways according to the wavelengths via filters. The number of photons, which relates to the intensity of the luminescence, for each wavelength range can be detected by a detector from which the electronic signal is passed through a variety of circuits and may be presented as a data set saved in memory. This detection process is based on the evaluation of signal intensity in a single optical band; therefore, without signal separation, it is difficult to identify the nature of the component. The fluorescence emission of almost all organic fluorochromes is broad, making it difficult to measure the emission intensity of an individual fluorescence label to the exclusion of another. This is the ultimate limitation of current systems. Accordingly, there is a need for a system that provides a spectral signature of the luminescent emission from particles and materials.

SUMMARY

A spectral detection system may include an observation region where a targeted sample luminesces when excited by a light source, a multi-channel photodetector array that has a plurality of photodetectors, each photodetector may receive a particular band of light from a spectrum of light collected from the observation region. The system may include a light-dispersion element that disperses the luminescence collected from the observation region and projects the spectrum onto photodetectors in the photodetector array, and a multi-channel collection system configured to receive a signal in parallel from each photodetector in the multi-channel photodetector array upon reception of a triggering signal. The multi-channel collection system may digitize the signal into a multi-bit word digital signal, process the digital signal, form a spectral signature by combining each of the multi-bit digital signal, and transmit the spectral signature. A processor may receive the spectral signature and further process the spectral signature and store the spectral signature for subsequent analysis. The processor may compare the spectral signature to a set of known spectral signatures before a next spectral signature is transmitted from the multi-channel collection system, the transmission from the multi-channel collection system may occur at a rate of about 1000 events per second.

A spectral detection system may include a flow chamber having an observation region where a biological particle flows in a fluid and is interrogated. A light source may irradiate the observation region, exciting and interrogating the biological particle, the biological particle luminesces and emitting a characteristic spectrum. The system may include a scattered-light detector that receives light scattered by the biological particle when the particle enters the observation region of the instrument and the scattered-light detector may transmit a triggering signal. The system may have a multi-channel photodetector array that has a plurality of photodetectors, each photodetector receiving a particular band of light from the spectrum emitted from the targeted biological particle. The system may include a light-dispersion element that disperses the luminescence and projects the particular band of light from the spectrum onto each photodetector in the photodetector array. A multi-channel collection system may be included that is configured to receive signals in parallel from each photodetector in the multi-channel photodetector array upon the triggering signal, digitizes the signals into a multi-bit word digital signals, processes the signals, forms spectral signatures, and transmits the spectral signatures. A processor may receive the spectral signatures, may further process the spectral signatures, and may store the spectral signatures for subsequent analysis and may compare the spectral signatures to a set of known spectral signatures. The processor may compare the spectral signature to a set of known spectral signatures before the next triggering signal is received from the scatter detector, the triggering may occur at a rate of about 1000 events per second. The triggering also may occur at a rate of about 10,000 events per second.

The system may include a flow cytometry chamber that transports a biological particle in a fluid past the spectral detection system, the biological particle may be combined with one or more of a staining agent, a marker, and a tag. The combination of the biological particle and the staining agent, the marker, and/or the tag may provide luminescence when excited by the light source.

A method for detecting spectral signatures in a high-speed flow cytometry may include flowing a biological particle in a fluid through a flow chamber having an observation region where a biological particle is interrogated. The observation region may be irradiated with light from a light source for interrogating and exciting the biological particle. Upon excitation, the biological particle may luminesce and emit a spectrum of light. The light or luminescence from the biological particle may be dispersed. When the light is dispersed, a particular band of light from the spectrum may be projected onto a photodetector in a multi-channel photodetector array. The photodetector may receive a particular band of light from the spectrum and transmit an electrical signal. The method may include forming a spectral signature in a multi-channel collection system. The multi-channel collection system may be configured to receive signals in parallel from each photodetector in the multi-channel photodetector array upon receiving a triggering signal. The multi-channel collection system may digitize the signals into multi-bit word digital signals, process the signals, and transmit the spectral signatures to a processor. The method may include comparing the spectral signature to a set of known spectral signatures in a processor configured to receive the spectral signatures, further process the spectral signal, store the spectral signal for subsequent analysis before the next triggering signal is received from a scatter detector, the triggering signal occurring more than about 1000 events per second.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like-referenced numerals designate corresponding parts throughout the different views.

DETAILED DESCRIPTION OF THE PREFERRED EMBODIMENTS

Figure 1:
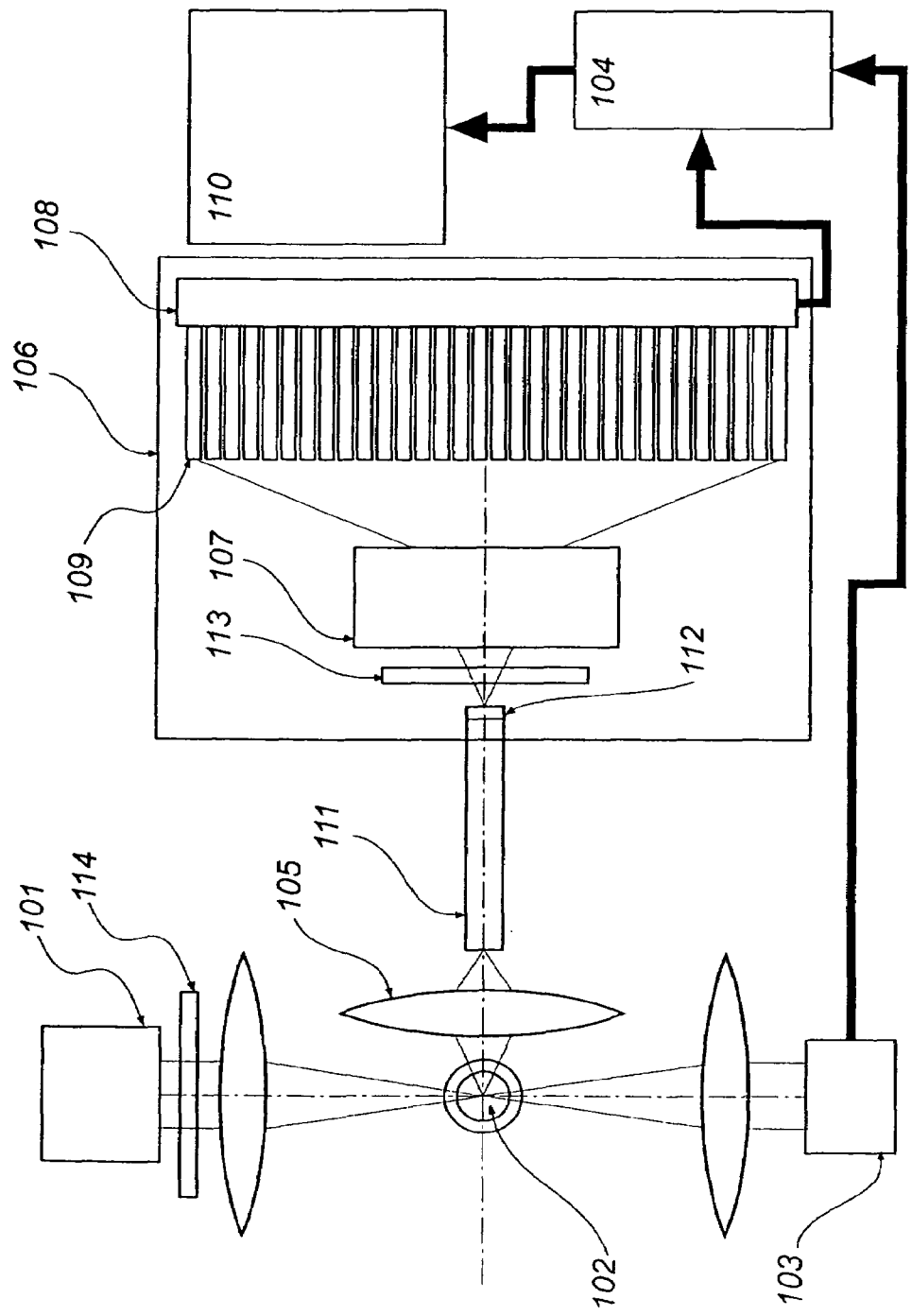
FIG. 1 is a block diagram of a spectral detection system.

A spectral detection system may include a light source for exciting a targeted sample. The targeted sample may be a crystalline structure or a micro-particle that will luminesce. The micro-particle may be a small biological particle that is about 60 µm or less. A micro-particle may include a biological particle either alone or in combination with a marker, a tag or a stain. The biological particle may be a human, animal, or plant cell, a bacterium, a virus, etc. Luminescence may include any means that is known or becomes known suitable for exciting the targeted sample. For example, luminescence may include fluorescence, phosphorescence, or chemiluminescence. The micro-particle may be sampled in an observation region of a flow cytometer where the particle is detected. The stain, either organic or inorganic, or a luminescent protein may, be used to tag or mark the micro-particle. The marker or tag may luminesce when irradiated. The marker or tag may exhibit a characteristic spectrum of luminescence, because of its physical structure, or the marker may exhibit a particular spectrum when combined with a specimen. The tag may take the form of nanocrystals (i.e. quantum dots) that luminesce, producing a characteristic spectrum determined by their composition and dimensions.

The luminescence, or fluorescence, from the targeted sample may be collected at an observation region and directed to a detector system. A fiber-optics cable may be used to guide the luminescence obtained from the targeted sample to the detector system. The luminescence signal may be directed to a light-dispersion element such as a grating that disperses the light into a spectrum. The detection system may be a multi-channel photodetector array, where each photodetector in the array receives a small component or band of the dispersed spectrum. When a photodetector receives its particular band of the spectrum, it transmits a signal to a multi-channel collection system that receives signals from all of the channels of the photodetector in parallel, digitizes the signals, and processes the signals to form a spectral signature. The spectral signature may be sent to a processor to be compared with known spectral signatures for a particular specimen of interest or stored in a memory for further processing. The multi-channel collection system may be triggered to sample an event at a regularly timed interval, or upon a luminescence or scatter occurrence in an observation region of a flow cytometer where the micro-particle may be detected.

The luminescence may occur when the light source stimulates a targeted sample. In an example that incorporates a flow cytometry fluidics arrangement, a biological particle in carrier liquid may flow past the light source and luminescence detectors. The biological particle may luminesce, or fluoresce, as a result of the light source having targeted and stimulated the intrinsic fluorochromes of the particle, or any attached tag or marker. A scatter detector may sense an occurrence of a particle in the detection region by collecting light scattered by the particle. The signal from the scatter detector may be transmitted to a multi-channel collection system, and may be used as electronic triggering signal to synchronize collection of luminescence. The scatter detector may be a separate device or one of the photodetectors in the multi-channel photodetector array that may be used for this purpose. Upon reception of the triggering signal, luminescence light is collected, the signals are processed, and a spectral signature is then formed for immediate or future analysis.

FIG. 1 is a block diagram of a multi-spectral detector 100. A light source 101 is directed to an observation region 102 when a targeted sample may be present for a short period of time while flowing through the flow chamber. The observation region 102 may be a small region of the flow chamber where the light source 101, a light-scatter detector 103, and luminescence collector 105 may be located. The targeted sample may luminesce, and the luminescence signal may be emitted in all directions. Not all of the light from the light source may be absorbed by the sample. Some of the incident light may be scattered by the particle as the particle flows through the observation region 102. A light-scatter detector 103 may collect a portion of the scattered light, generate a signal, and transmit the signal to a multi-channel collection system 104 that is coupled to the scatter detector 103 and multi-channel photodetector array 108. A light collector 105 such as a lens may be connected to an optical cable which may be connected to a housing 106. The housing 106 may contain a light-dispersion element 107. The light-dispersion element 107 may be in proximity to a photodetector array 108 that has multiple photodetectors. The proximity of the dispersion element 107 to the photodetector array 108 may be adjusted so that the spectrum is projected onto the array to allow each photodetector 109 in the photodetector array 108 to receive a portion of the spectrum. Each photodetector in the photodetector array is connected in parallel to the multi-channel collection system 104. The multi-channel collection system 104 may contain a high-speed digital signal processor ("DSP") for processing, comparing and analyzing signals. The multi-channel data collection system 104 is connected to a processor 110 for further processing of signals and data storage. The processor 110 may be located in a computer. The processor 110 may be a microprocessor, a microcomputer, or even a computer.

When a targeted sample 102 is excited by the light source 101, the targeted sample may luminesce. The targeted sample may be in an observation region 102 where the light source 101 is directed. The observation region 102 may be that portion of a flow cytometry chamber accessible to the light collector 105, the light source 101, and the detector 103.

The light source 101 may be any known light-source suitable for excitation of the target material. For example, the light source 101 may be a laser or a light emitting diode ("LED") that excites the targeted material to luminesce or fluoresce. The laser may have a multiple number of excitation wavelengths or a single wavelength. The laser may be any gas laser, solid-state laser, semiconductor diode laser, or dye laser. The light source may include a combination of semiconductor diode lasers of any wavelength with each diode having a different wavelength. A band-pass filter 114 may be placed in front of the laser. If the laser produces more than one line, the unwanted line may be filtered out before it reaches the sample.

The targeted sample 102 may be a biological particle. The biological particle may be stained by a dye that adheres or bonds to the particle. The biological particles may be blood cells, human or animal tissue, infectious agents, bacteria, viruses, yeast, protozoa, or other biological matter. The biological particle may also include a carrier. The carrier may be a small bead which has a surface to which the biological material attaches. The biological particle may also contain a porous carrier bead, which contains biological material inside the pores of the bead. The biological particles may be agents used in biological warfare. The detection of such biological particles may be rapid so that a response by health and public officials may be effected to isolate and quarantine the infected regions.

In flow cytometry, the biological particles may be confined to the center of a flowing stream of fluid through hydrodynamic focusing using a sheath fluid. The biological particles may also flow in a stream of fluid without the sheath. The carrier fluid may transport biological particles through the observation region 102, allowing the collection of luminescence.

Figure 2:
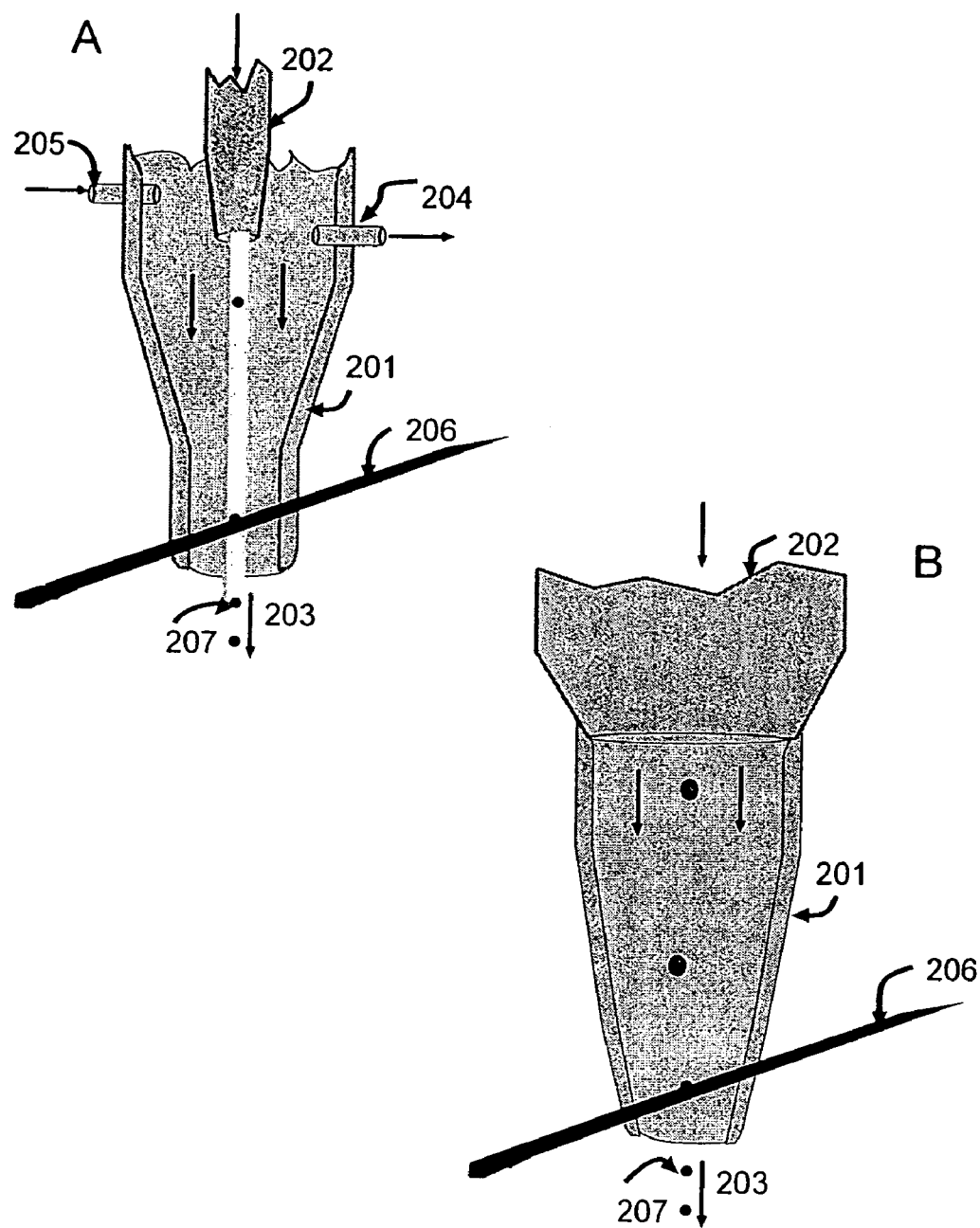
FIG. 2 is a diagram of two flow chambers.

FIG. 2 shows two representations of flow chambers 201. The flow chamber in A 201 may allow a particle 207 to enter the chamber 201 via a sample tube 202. The particle may flow through the chamber exiting the chamber at an exit port 203. As the particle flows through the flow chamber a laser beam 206 may intersect the chamber at an observation region of the flow tube where the particle may be irradiated with light. In A 201, the light source 101 is the laser beam 206. A sheath of fluid may direct the particles to a particular point in the observation region so that they may be interrogated by the laser. This process may be called hydrodynamic focusing. The sheath fluid may enter the chamber at a port 205. The sheath of fluid may flow through the chamber leaving the chamber at exit port 203. Excess fluid may vacate the chamber 204.

Alternative B shows a flow chamber 201 with a sample injection tube 202 from which fluid may flow toward the exit 203 carrying particles 207. As each particle moves through the flow chamber, a laser beam 206 may intersect the chamber and irradiate the particle. Alternative B does not use sheath fluid and hydrodynamic focusing.

To facilitate the detection of the biological particles for analysis and classification, various organic and inorganic luminescence tags may be attached to the biological compounds of the particle. Each fluorochrome may have a unique excitation and emission property to provide identification of a tagged biological particle. The markers or tags may include organic or inorganic stains. The markers or tags may also include compounds that have direct energy band-gaps, such as those materials that are used to create quantum dots. A quantum dot is generally formed in direct energy band-gap material and the quantum dot is a form of a specialized quantum well where quantum field effects have an influence on particles such as electrons. The arrangement of the quantum dot may luminesce with a specific wavelength. If a luminescent marker or a tag selectively attaches to a particular biological element in a biological particle, then the presence of the biological element may be readily identified as it flows past the light source 101 and the detector 103 and the light collector 105.

Quantum dot-based tags may include materials that are crystalline with varying characteristics. The quantum dots may be formed from alloys having specific band-gaps and electrical characteristics. The materials forming the alloys may be compound semiconductors and when they are formed in the correct combination, they may form light sources such as semiconductor lasers or light emitting diodes or light detectors. The emission spectra may be tuned to a desired wavelength by the use of different materials such as aluminum gallium nitride ("AlGaN") for the ultraviolet and blue spectrum regions and gallium arsenide ("GaAs") for the near infrared region. Further adjustments may be made by adjusting the size of the quantum dot. When these alloys are excited with a light source, they may photoluminesce at a particular wavelength dependent upon the dimensions of the various structural layers and the energy band-gap of the layers.

After the targeted sample is illuminated by the light source 101, the targeted sample may scatter incident light while in the observation region 102. A scatter detector 103 may detect the light scattered from the targeted sample. Upon detection, the scatter detector 103 will transmit a signal to the multi-channel collection system 104. The multi-channel collection system 104 may be a high-speed computer board with digital signal processors ("DSP") and analog-to-digital ("A/D") converters. The multi-channel collection system 104 may be installed in a computer, or a stand-alone specialized computer.

Figure 3:
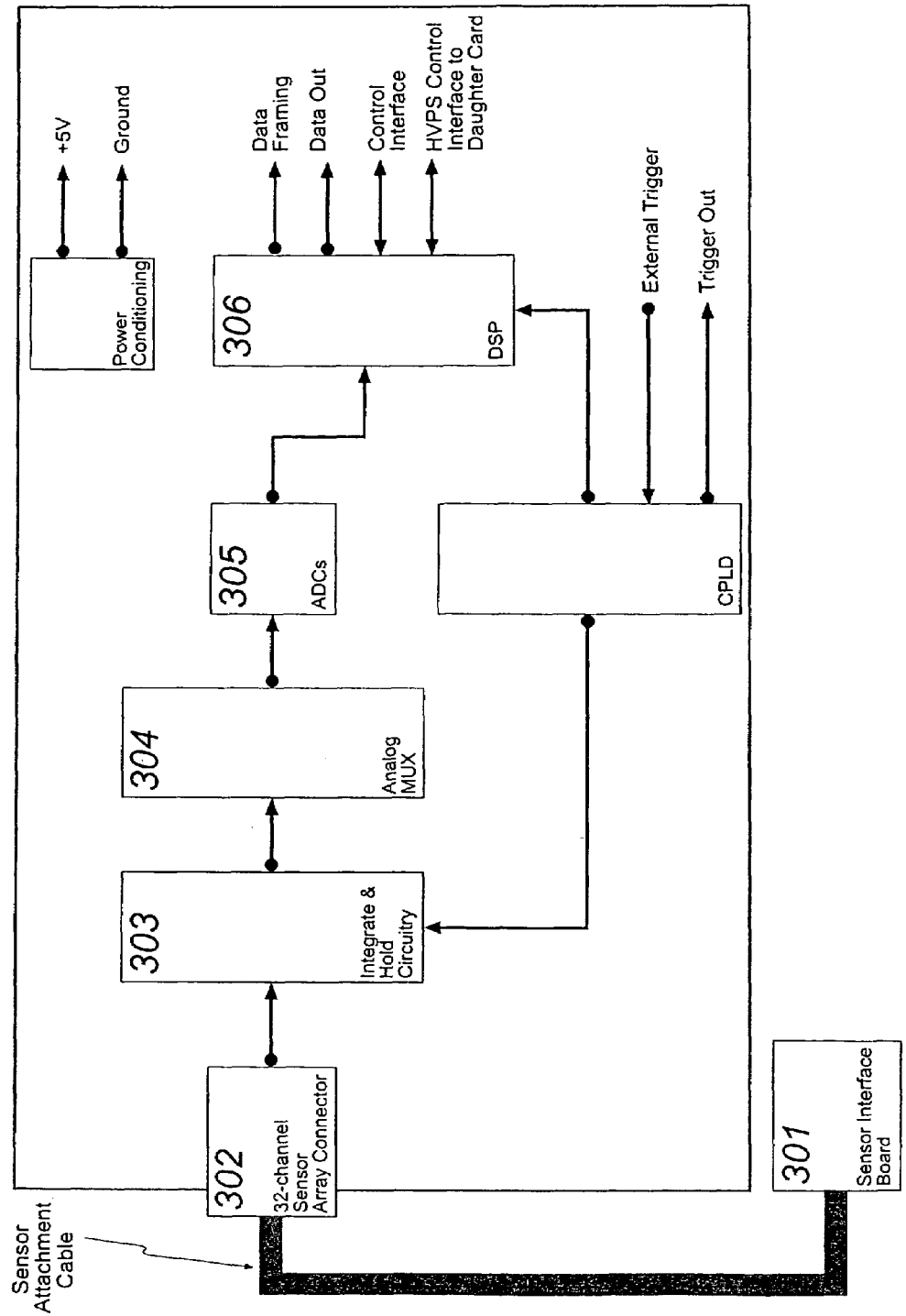
FIG. 3 is a block diagram of a multi-channel collection system.

FIG. 3 is a block diagram of a multi-channel collection system 104 that may receive the signals from a multi-channel photodetector array 108. The multi-channel collection system 104 may be a PhotoniQ-OEM Model 3214™ board that may be installed in a PC computer. The multi-channel collection system 104 may have as many input channels as there are channels in the multi-channel photodetector array 109. A sensor interface board 301 may connect to the multi-channel photodetector array 108. The array sensor interface 301 may connect to the multi-channel collection system 104 through an array sensor connector 302. The array sensor connector 302 may have 32 channels or it may have fewer or more channels depending upon the application and the multi-channel photodetector array 108. The array sensor connector 302 may connect to an integrate-and-hold circuit 303. The integrate-and-hold circuit 303 may connect to an analog multiplexer ("MUX") 304 with the output of the MUX 304 channeling the analog signal to an A/D converter 305. The output of the A/D converter 305 may connect to a digital signal processor ("DSP") 306. The DSP 306 may connect to a processor 110. The DSP 306 may also connect to a complex programmable logic device ("CPLD") 307. The multi-channel collection electronics 104 may be a stand-alone system or it may be integrated onto a board such as the PhotoniQ-OEM Model 3214™.

When the scatter detector 103 sends a signal to the array sensor 301 the CPLD 307 may utilize the signal as an external trigger. The use of the external trigger may incur some synchronization delay. The synchronization delay may be about 15 nsec. The CPLD 307 may send a signal to the integrate-and-hold circuit 303 where the signals from the detector array 108 are received and captured. The analog MUX 304 will send the signals to the A/D converter 305 for digitizing the signal into multi-bit words. The multi-bit word may have a length of 8, 16, or 32 bits. Other bit word lengths may be used as well. The length of the bit word is not a limitation of the multi-channel collection electronics 104. The output of the A/D converter 305 may be attached to the DSP 306. The DSP 306 may condition the multi-bit words into a spectral signature for transmission to the processor 110 where the spectral signature is analyzed against known signatures for the detection and identification of the targeted sample 102. The array sensor may transmit the multi-bit words to a processor 110, computer or other processing device either serially or in parallel. For high-speed analysis, it may be preferable to use parallel transmission, but a very high-speed communication circuit may adequately provide for the serial transmission of data For instance, the multi-channel data collection electronics 104 may allow a new event to occur about every 13 μs or even more often than that. Thus, after receiving an event trigger, the multi-channel collection electronics 104 may have integrated 32 channels simultaneously, digitized the results, and transmitted the 32 16-bit measurements out the data port.

The synchronization delay of the measured intensity of light received at a photodetector 109 and the triggering signal may result in an intensity that is somewhat reduced from the time that the scatter detector 103 initially responded to the scattered light. The synchronization delay may be less than about 15 nanoseconds ("nsec."). Since the signal from the photodetectors are read and processed together, it is the parallel combination of the individual signals that may be analyzed. The signals may be combined and mapped according to the wavelength, forming a spectral fingerprint of the combined signal.

Figure 4:
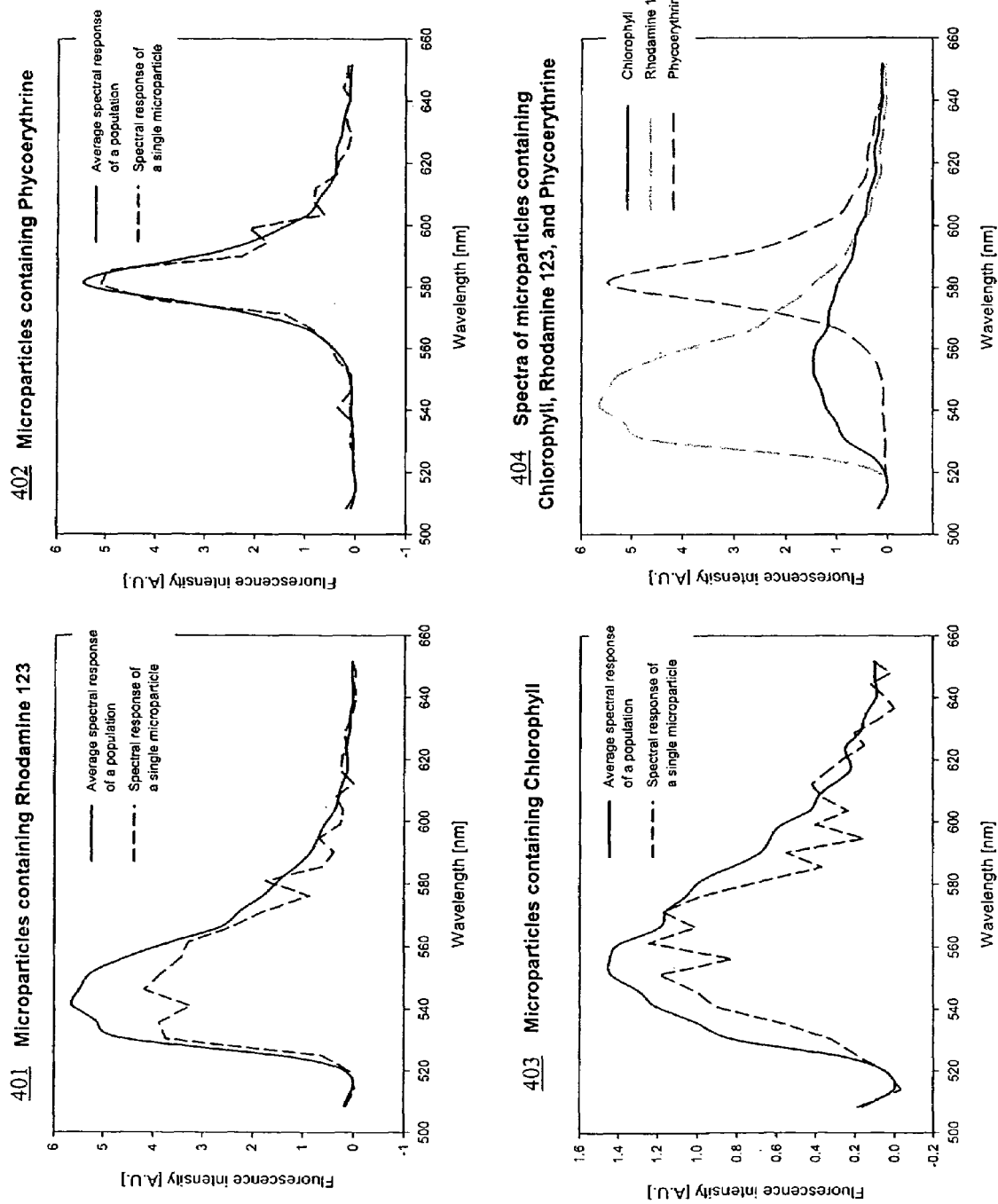
FIG. 4 is a series of views of spectral responses.

Examples of spectral signatures for particles that have been analyzed are shown in FIG. 4. The combination of the luminescence signals collected by the multi-channel photodetector array 108 forms the spectral signatures. The spectral signature of particles stained with Rhodamine 123, Phycoerithrin, and Chlorophyll are shown in views 401, 402 and 403, respectively. The particles were excited by an argon-ion laser with an excitation wavelength of about 488 nm to obtain the luminescence. The luminescence displayed a spectral signature that was dependent on the stains. As seen in the views 404, 405, and 406, significant spectral overlap occurred in many of the channels. View 404 shows a total overlap of the Chlorophyll and Rhodamine 123 spectra. The overlap may preclude non-multispectral detection and discrimination of these particles when a mixture of particles is analyzed. Even for modestly overlapping stains like Rhodamine 123 and Phycoerythrine such an analysis may not be performed without the use of compensation. However, upon collection of the spectral data from the multi-channel photodetector array 108, complete separation of the different dyed particles may be possible in the absence of the compensation procedure. Some photodetectors 109 in an array may receive the same amount of light even though the light originates from particles, each particle stained with Chlorophyll, Rhodamine 123, or Phycoerithrin. The characteristic spectral signatures for particles stained these three stains are different.

Figure 5:
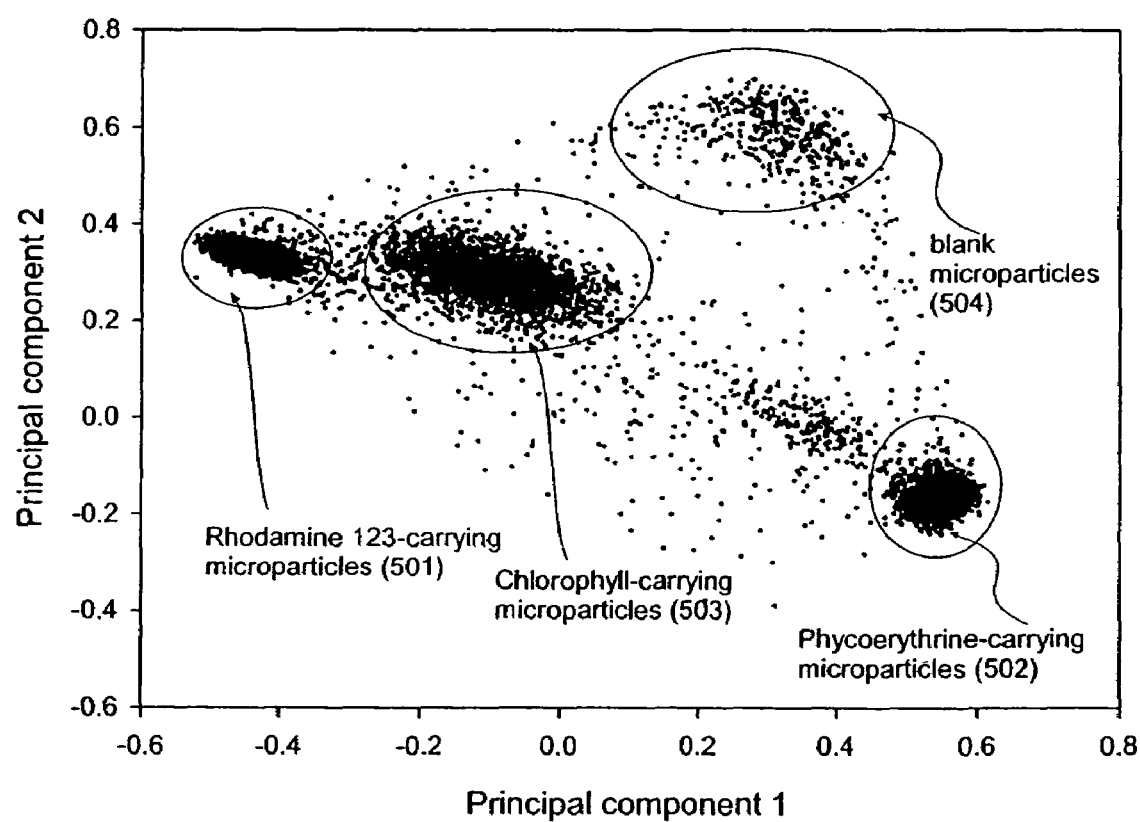
FIG. 5 is a classification diagram of particle spectral responses.
Figure 6:
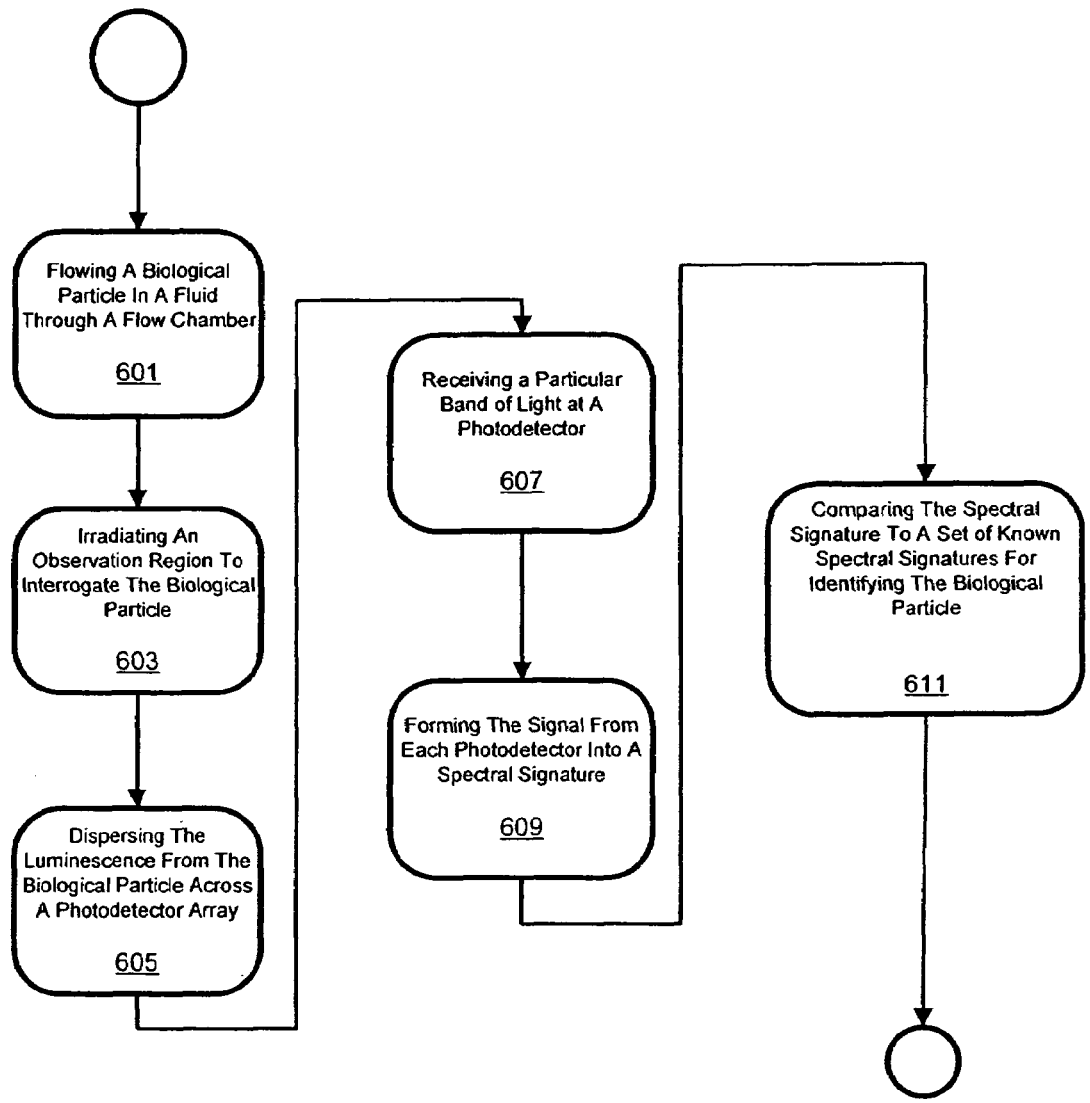
FIG. 6 is a flow for a method of detecting spectral signatures in high-speed flow cytometry.

An analysis and classification of these particles using principal component analysis ("PCA") is shown in FIG. 5. The particles that are stained with Rhodamine 123 (501), Phycoerythrin (502), or Chlorophyll (503) and the unstained particles (504), were clearly separated and identified. The spectral signature of each particle may be collected, in the presence of spectral overlap and a lack of a compensation, to achieve such a level of separation as demonstrated in FIG. 5. Such an analysis may be performed in real time or it may be conducted during subsequent off-line processing.

A spectral signature of a particle may be collected in real time and the spectral signature will be used for classifying that particle. As stated above, the spectral signature may be determined even in the absence of spectral compensation. Spectral compensation has been performed in multi-color cytometry because of the spectral overlap that occurs in some other cytometry systems. Spectral compensation may be used to separate the individual intensity-based signals that are the basis of those systems. Spectral compensation may be advantageous prior to making any classification of a particle. In particular, multiple spectra may be collected and analyzed by the processor 110 without spectral compensation applied to the collected signal.

The luminescence of the targeted particle may be collected and focused by a light collector or lens 105. The lens 105 may focus the collected light into a fiber 111 and guide the light to a slit 112 where the light is directed to a light-dispersion element 107. The fiber 111 may not be necessary and in some applications it may be excluded. The light collector 105 may be integral to the detector housing 106 or it may be omitted completely. On either side of the slit, a beam-blocking filter may be present. The beam-blocking filter may be a filter that blocks a band of light used to excite luminescence. The narrow band of light that is blocked may be the primary wavelength line of the light source 101. The narrow band of light may correspond to a lasing wavelength for the light source 101 if a laser is used or it may correspond to the center wavelength of an LED. Where a laser is used with several lasing wavelengths, the beam-blocking filter may have capability to block each lasing wavelength. However, multiple beam-blocking filters may be used in combination, one for each of the wavelengths. The more common lasing wavelengths may include wavelengths of about 405 nm, 488 nm, 514 nm, 532 nm, 568 nm, 633 nm, and 647 nm. Semiconductor lasers and LEDs may be obtained for almost any wavelength from the ultraviolet to the far infrared range. Beam-blocking filters utilized with such lasers and LEDs may correspond to the wavelength of the light source 101 which is used to excite the luminescence of the sample.

The light-dispersion element 107 may be a diffraction grating, or a prism that may spectrally separate the wavelength, dispersing the light and projecting it across the multi-channel photodetector array 108. In one example, the light-dispersing element 107 will be aligned, so the spectrum is projected evenly across the multi-channel photodetector array 108, although the spectrum may be aligned differently depending upon the application. The spectral region that may be detected with the detection system 100 may range from about 400 nm to about 880 nm. The detection system 100 may be designed for other wavelengths and may depend upon the type and wavelength sensitivity of the multi-channel photodetector array 108.

The multi-channel photodetector array 108 may have multiple photodetectors 109. The multi-channel photodetector array may have thirty-two or more photodetectors. Other, similar photodetector arrays may become available having as many as forty-eight or even sixty-four photodetectors. More detectors in the array may mean that a wider spectral range may be detected. In other applications, a finer range of detection giving better spectral resolution may be achieved. In a preferred embodiment, the multichannel photodetector array 108 may have thirty-two anodes, such as a Hamamatsu® H7260 or a H7259 series of 32-channel photomultiplier tubes ("PMT"). The spectral resolution of the detector may be about 5 to about 10 nm. The multi-channel data system 104 receiving the signals from the multi-channel photodetector array 108 may have the same number of channels as the multi-channel photodetector array 108, one channel for each photodetector 109. The photodetector 109 may be a photodiode, an avalanche diode, or a photomultiplier tube. A photodetector 109 may be any electro-optical device that upon illumination transmits an electrical signal provided that the sensitivity of the photodetector is high enough.

A processor 110 may receive the spectral signatures from the multi-channel collection system 104. The spectral signatures may be analyzed, and compared with other known signatures. Known computer algorithms for pattern matching may be used to match the spectral signature. The process of analysis and matching may be run off-line or during the data collection. Since the multi-channel collection system may be triggered about every 10 microseconds ("μsec") or even faster, the pattern-matching algorithm operates in an optimal fashion, preferably within the environment of a real-time operating system.

Spectral data sets or spectral signatures may be collected by screening biological particles tagged with various organic or inorganic stains, or nanocrystals. The spectral signatures may be subsequently classified into categories using multivariate statistical analysis. A number of multivariate statistical methods may be used ranging from linear decomposition (i.e. Principal Components Analysis, Correspondence Analysis, Karhunen-Loeve transformation) through Independent Component Analysis to nonlinear transformations (i.e., neural networks).

In a preferred embodiment the processor may use Principal Component Analysis to separate and classify microparticles. However, the method of choice may depend on the particular application of the spectral screening technology.

In a preferred embodiment, the spectral detection system may be used in a typical flow cytometry apparatus. The process of flow cytometry may evaluate biological particles. The biological particles may include bacteria, human tissue, blood cells, and many other biological specimens. By varying the light-collection portion of the system and/or the fluidics system, other embodiments may become evident to one skilled in the art.

For instance, the light source may be directed to a crystalline structure that is being disposed in a reactor. A light-collection system may be mounted on a port to detect any emission from the targeted material. Where high temperatures are used within the chamber, an infrared filter may be used to filter the infrared radiation. The return of a spectral signature from the luminescence of the targeted sample representing the current condition of the product may be returned in real-time to make adjustments to the growth parameters to affect the proper material.

For example, a particular wavelength may be desired in a quantum dot. The quantum dots are commonly grown in a vapor-deposition process. The deposition of the materials surrounding the quantum dot may play a role in forming the predominant energy levels in the quantum dot. Monitoring the deposition in real-time with the light-collection system attached to the port may assist in real time adjustments to the deposition process. The manufacturing process may be continuously adjusted as the layers of the structure are deposited. Once the desired quantum dot is produced, the quantum dot may be used as a tag in a flow cytometry multi-spectral detector. The quantum dot-based tag may preferentially attach to some biological specimens and not others. When the quantum dot tag does preferentially attach, the biological element will be readily identified.

Other manufacturing processes may utilize the multi-spectral detector for real-time monitoring of the processes where the measurement of light may be advantageous and the reception of a spectral signature is indicative of the on-going process. Those skilled in the art will realize how to excite the material and collect the emitted light from the fluorescence or photoluminescence.

In one application, a method for detecting a biological particle may include flowing (act 601) a biological particle through a flow cytometry channel 102. The flow cytometry channel may have an observation region for irradiating biological particles or micro-particles. A biological micro-particle may be about 60 μm or less in size. The observation region may be irradiated (act 603) with light from a light source 101. The light source 101 may be a diode laser or an LED. The light may be scattered by a biological particle flowing through the channel 102. The scattered light maybe detected by a scattered-light detector 103 that will provide a triggering signal.

The biological particle may luminesce when it is excited by the light source 101. The light may be collected by a lens 105 and focused to an optical fiber and transmitted to a slit where the light enters a housing and is dispersed (act 605) with a light-dispersion element. The light-dispersion element may disperse the luminescence and project a particular band of light to a photodetector in a photodetector array. The photodetector array will have multiple photodetectors in the array, each photodetector in the array may receive (act 607) a particular band of light from the luminescence.

Each photodiode in the multi-channel photodiode array 108 will transmit an electrical signal when it detects the particular band of light. The signal may be received at a multi-channel collection system 104. The multi-channel collection system 104 may form (act 609) the signals received from the photodetectors into a combined signal that reveals a spectral signature. The multi-channel collection system 104 may be configured to receive, digitize, and process the signal, thus forming (act 609) the spectral signature. The multi-channel collection system 104 may include an integrate and hold circuit 303, an analog MUX 304, an A/D converter 305, and a DSP 306. The multi-channel collection system 104 may receive a triggering signal from a light-scatter detector 103. When the triggering signal is received by the system 104, the signals from the photodetector array 108 will be received and processed at the integrate and hold circuit 303. The developed signals will be further processed in the system 104 forming (act 611) the spectral signature. Once the spectral signature is formed it may be transmitted to a processor 110 where the spectral signature may be further processed.

The processor may compare (act 611) the spectral signature upon reception to a set of known spectral signatures to identify the biological particle. The set of known spectral signatures may be stored in a memory. The processor may not immediately compare the spectral signatures but may wait and do the comparison in a subsequent analysis.

The comparing (act 611) may include spectral data sets or spectral signatures collected by screening biological particles tagged with various organic or inorganic stains, or nanocrystals. The spectral signatures may be subsequently classified into categories using multivariate statistical analysis. A number of multivariate statistical methods may be used ranging from linear decomposition through Independent Component Analysis to nonlinear transformations.

The comparing (act 611) may be done at data rates where 1000 events per second occur. This corresponds to at least 1000 events where biological particles scatter light and a full analysis of the spectral signature is collected and compared to known biological particles. Further, the comparison may operate at data rates capable of 10,000 events per second. The high speed capability may allow the multi-channel detection system to receive spectral data at about 10,000 events per second.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A spectral detection system for detection, analysis, and classification of micro-particles, comprising:
   an observation region, where a targeted sample luminesces when excited by a light source;
   a multi-channel photodetector array having a plurality of photodetectors, each photodetector configured to receive a particular band of light from a spectrum of light collected from the observation region;
   a light-dispersion element configured to disperse the luminescence collected from the observation region and project the spectrum onto photodetectors in the photodetector array;
   a detector configured to detect the luminescence and transmit a triggering signal upon detection;
   a multi-channel collection system configured to receive a signal in parallel from each photodetector in the multi-channel photodetector array upon the triggering signal, digitize the signal into a multi-bit word digital signal, process the digital signal, form a spectral signature by combining each digital signal, and transmit the spectral signature; and
   a processor configured to receive the spectral signature and process the spectral signature and store the spectral signature for a subsequent analysis.

2. The system of claim 1, where the targeted sample is a biological particle in a flow cytometry apparatus that transports the biological particle in a fluid past the spectral detection system, the biological particle combined with one or more of a staining agent, a marker, and a tag, the combination providing luminescence when excited by the light source.

3. The system of claim 2, where the flow cytometry apparatus comprises a sheath of fluid capable of directing the biological particle to a particular location in the observation region.

4. The system of claim 1, where the targeted sample is a crystalline structure, capable of luminescence when excited by the light source.

5. The system of claim 4, where the crystalline structure comprises a structure on which crystalline layers of different band-gaps may be deposited, the crystalline layers emitting luminescence when excited by the light source.

6. The system of claim 4, where the targeted sample provides a spectral signature of an energy band-gap, the energy band gap being determined by a physical arrangement of materials.

7. The system of claim 1, where the light source is one of a light emitting diode and a laser.

8. The system of claim 1, where the light-dispersing element is one of a prism and a diffraction grating.

9. The system of claim 1, where the photodetector array comprises at least thirty-two photodetectors.

10. The system of claim 9, where the photodetector array is a multi-anode photomultiplier array.

11. The system of claim 1, where the multi-channel photodetector array detects wavelengths from about 400 nm to about 880 nm.

12. The system of claim 1, further comprising a band-blocking filter for blocking the excitation wavelength of the light source.

13. The system of claim 12, where the band-blocking filter blocks at least one wavelength region at about 405 nm, about 488 nm, about 514 nm, about 532 nm, about 568 nm, about 633 nm, and about 647 nm.

14. The system of claim 1, where the triggering occurs at regularly timed intervals.

15. The system of claim 1, where the triggering occurs at greater than about 1000 times per second.

16. The system of claim 1, where the processor performs the subsequent analysis upon receiving the spectral signature.

17. The system of claim 16, where the processor compares the spectral signature to a set of known spectral signatures before a next spectral signature is transmitted from the multi-channel collection system, the transmission from the multi-channel collection system occurring at a rate of about 1000 events per second.

18. A spectral detection system for flow cytometry, comprising:
   a flow chamber having an observation region where a biological particle flows in a fluid and is interrogated;
   a light source configured to irradiate the observation region, where the biological particle luminesces and emits a spectrum;
   a scattered-light detector configured to receive light scattered by the biological particle when the particle enters the detection region of the instrument and transmit a triggering signal;
   a multi-channel photodetector array having a plurality of photodetectors, each photodetector configured to receive a particular band of light from the spectrum emitted from the targeted biological particle;
   a light-dispersion element configured to disperse the luminescence and project the particular band of light from the spectrum onto each photodetector in the photodetector array;
   a multi-channel collection system configured to receive a signal in parallel from each photodetector in the multi-channel photodetector array upon the triggering signal, digitize the signal into a multi-bit word digital signal, process the signal, form a spectral signature, and transmit the spectral signature; and a processor configured to receive the spectral signature, further process the spectral signature, store the spectral signature for subsequent analysis, and compare the spectral signature to a set of known spectral signatures.

19. The system of claim 18, containing a processor that receives the spectral signature and compares the spectral signature to a set of known spectral signatures before a next triggering signal is received from the scatter detector, the triggering occurring at a rate of more than about 1000 events per second.

20. The system of claim 18, where the targeted biological sample includes a stain connected to the targeted biological sample and the stain exhibits a spectral signature when the targeted biological sample is excited by the light source.

21. The system of claim 18, where the targeted biological sample and a tag provide a spectral signature based upon an energy band-gap of a compound in the tag.

22. The system of claim 21, where the energy band-gap is determined by a physical arrangement of materials in the tag.

23. The system of claim 18, where the multi-channel detection system receives spectral data at about 10,000 events per second.

24. The system of claim 18, where the light source is one of a light emitting diode and a laser.

25. The system of claim 18, further comprising an optical blocking filter for removing a particular wavelength.

26. A spectral detection system for high-speed flow cytometry, comprising:
   a flow chamber having an observation region where a biological particle flows in a fluid and is interrogated;
   a light source configured to irradiate the observation region that excites and interrogates the biological particle, the biological particle luminesces and emits a spectrum;
   a scattered-light detector configured to receive light scattered by the biological particle when the particle enters the detection region of the instrument and configured to transmit a triggering signal;
   a multi-channel photodetector array having a plurality of photodetectors, each photodetector configured to receive a particular band of light from the spectrum emitted from the targeted biological particle;
   a light dispersion element that disperses the luminescence and projects the particular band of light from the spectrum onto each photodetector in the photodetector array;
   a multi-channel collection system configured to receive a signal in parallel from each photodetector in the multi-channel photodetector array upon the triggering signal, digitize the signal into a multi-bit word digital signal, process the signal, form a spectral signature, and transmit the spectral signature; and
   a processor that receives the spectral signature, processes the spectral signal further, and stores the spectral signature for subsequent analysis and compares the spectral signature to a set of known spectral signatures before the next triggering signal is received from the scatter detector, the triggering occurring more than about 1000 events per second.

27. The system of claim 26, where the biological particle includes a stain connected to the biological particle and the stain exhibits a spectral signature when the biological particle is excited by the light source.

28. The system of claim 27, where the biological particle and a tag attached to the biological particle provide a spectral signature.

29. The system of claim 28, where the spectral signature of the biological particle and tag is determined by a physical arrangement of materials in the tag.

30. The system of claim 27, where the multi-channel detection system receives spectral data at about 10,000 events per second.

31. The system of claim 26, where the light source is one of an LED and a laser.

32. The system of claim 26, further comprising an optical blocking filter for removing a particular wavelength.

33. A method for detecting spectral signatures in high-speed flow cytometry, comprising:
   flowing a biological particle in a fluid through a flow chamber having an observation region where a biological particle is interrogated;
   irradiating the biological particle with light in the observation region that excites and interrogates the biological particle, the biological particle luminescing and emitting a spectrum;
   transmitting a triggering signal upon detection of the luminescence;
   dispersing the luminescence and projecting a particular band of light from the spectrum onto a photodetector in a multi-channel photodetector array;
   receiving a particular band of light from the spectrum at the photodetector in the multi-channel photodetector array and transmitting a signal;
   forming a spectral signature in a multi-channel collection system configured to receive the signal in parallel from each photodetector in the multi-channel photodetector array upon receiving the triggering signal, digitize the signal into a multi-bit word digital signal, process the signal, and transmit the spectral signature; and
   comparing the spectral signature to a set of known spectral signatures in a processor configured to receive the spectral signature, further process the spectral signal, store the spectral signal for subsequent analysis before the next triggering signal is received from a light-scatter detector, the triggering signal occurring more than about 1000 events per second.

34. The method of claim 33, further comprising detecting scattered light from a biological particle and transmitting a triggering signal.

* * * * *